United States Patent
Tanaka et al.

[11] Patent Number: 5,841,001
[45] Date of Patent: Nov. 24, 1998

[54] PROCESS FOR THE PREPARATION OF OPTICALLY ACTIVE 2-HALO-1-(SUBSTITUTED PHENYL) ETHANOL

[75] Inventors: Ken Tanaka; Mari Yasuda; Makoto Ueda, all of Kanagawa, Japan

[73] Assignee: Mitsubishi Chemical Corporation, Tokyo, Japan

[21] Appl. No.: 808,853

[22] Filed: Feb. 28, 1997

[30] Foreign Application Priority Data

Feb. 28, 1996 [JP] Japan ................................. 8-041441

[51] Int. Cl.$^6$ .................... C07C 209/02; C07C 33/20; C07C 33/34
[52] U.S. Cl. .................... 568/812; 558/415; 558/418; 558/420; 558/425; 558/423; 562/493; 564/400; 564/401; 564/404; 568/725
[58] Field of Search .................... 568/812, 705; 558/415, 418, 420, 423, 425; 562/493; 564/400, 401, 404

[56] References Cited

FOREIGN PATENT DOCUMENTS 0735142  3/1996  European Pat. Off. .

OTHER PUBLICATIONS

Chemical Abstracts 116:40562, 1991.
Nieduzak, Tetrahedron: Asymmetry, vol 2(2), pp. 113–122, 1991.
Casreact #102: 184439, 1985.
Casreact #104: 168047, 1985.
Casreact #106: 18013, 1985.
Casreact #109:6342, 1988.
Casreact 117:131102, 1992.
Casreact #118:212177, 1993.
CASREACT 125:167489, 1996.
CHEMINFORMRX 199344084, 1993.
CHEMINFORMRX 199209060, 1992.
CHEMINFORMRX 199422086, 1994.
CHEMINFORMRX 199520038, 1995.
CHEMINFORMRX 199520059, 1995.
CHEMINFORMRX 199612182, 1996.
CASREACT 102: 184439, 1985.
CASREACT 103: 177665, 1985.
CASREACT 105:6658, 1985.
CASREACT 113:58884, 1989.
CASREACT 115:158610, 1991.
CASREACT 121:205392, 1994.
CASREACT 122: 160381, 1995.
CASREACT 122:291227, 1995.

*Primary Examiner*—John Kight
*Assistant Examiner*—D. Margaret M. Mach
*Attorney, Agent, or Firm*—Oblon, Spivak, McClelland, Maier & Neustadt, P.C.

[57] ABSTRACT

The present invention provides an industrially advantageous process for the preparation of an optically active 2-halo-1-(substituted phenyl)ethanol useful as medicines, agricultural chemicals or as intermediates thereof; and a simple process for the preparation of an optically active substituted styrene oxide or 2-amino-1-(substituted phenyl)ethanol useful as medicines, agricultural chemicals or intermediates thereof. A 2-halo-1-(substituted phenyl)ethanol represented by the following general formula (I) is allowed to contact, in the presence of a carboxylic anhydride, with an enzyme stereoselectively catalyzing ester interchange to produce an optically active 2-halo-1-(substituted phenyl)ethanol:

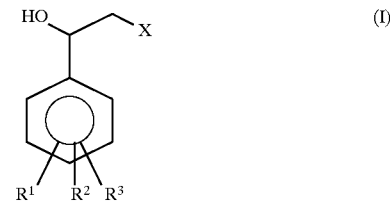

(wherein X represents a chlorine atom or a bromine atom, and $R^1$, $R^2$ and $R^3$ may be the same or different and each represent a hydrogen atom, a halogen atom, a $C_{1-5}$ alkyl group, a $C_{1-5}$ haloalkyl group, a $C_{1-5}$ alkoxy group, a cyano group or a nitro group, with the proviso that when two of $R^1$, $R^2$ and $R^3$ are alkyl groups or alkoxy groups, they may be combined together to form a ring and that all of $R^1$, $R^2$ and $R^3$ are not hydrogen atoms at the same time).

9 Claims, No Drawings

PROCESS FOR THE PREPARATION OF OPTICALLY ACTIVE 2-HALO-1-(SUBSTITUTED PHENYL) ETHANOL

FIELD OF THE INVENTION

The present invention relates to a process for the preparation of an optically active 2-halo-1-(substituted phenyl) ethanol.

More particularly, the present invention relates to a process for the efficient preparation of an optically active 2-halo-1-(substituted phenyl)ethanol (II) from a 2-halo-1-(substituted phenyl)ethanol (I) in the presence of a specific enzyme, a process for the simple preparation of an optically active substituted styrene oxide (IV) which comprises the treatment of the compound (II) with a base, and a process for the preparation of an optically active 2-amino-1-(substituted phenyl)ethanol (V) which comprises treating the compound (II) with a base to obtain an optically active substituted styrene oxide (IV) and then reacting the compound (IV) with an amine compound.

These compounds are useful as optically active medicines or agricultural chemicals or as intermediates for the synthesis thereof.

BACKGROUND OF THE INVENTION

As the process for the preparation of an optically active 2-halo-1-(substituted phenyl)ethanol and an optically active substituted styrene oxide, there have been known a process of subjecting 3-chlorophenacyl chloride to asymmetric borane reduction to produce an optically active 2-chloro-(3-chlorophenyl)ethanol and then subjecting the resulting optically active 2-chloro-(3-chlorophenyl)ethanol to ring-close to prepare an optically active 3-chlorostyrene oxide (J. Med. Chem., 35, 3081 (1992)) and a process of subjecting a substituted phenacyl halide to asymmetric reduction with a microorganism to produce an optically active 2-halo-1-(substituted phenyl)ethanol and then subjecting the resulting optically active 2-halo-1-(substituted phenyl)ethanol to ring-closure to prepare an optically active substituted styrene oxide (JP-A-4-218384 (The term "JP-A" as used herein means an "unexamined published Japanese patent application")).

However, the these preparation processes are disadvantageous in that they require the use of a highly lachrymatory and toxic substituted phenacyl halide, which causes difficulty in handling and waste disposal. Further, the former process is disadvantageous in (1) use of borane, which is expensive as a reaction reagent, is unstable, and is difficult to handle, (2) use of an expensive optically active ligand and (3) insufficient optical purity of the product, i.e. 85% ee. The latter process can give a product having a sufficient optical purity of 95% ee or more. However, this process is disadvantageous in that it can only be effected when the concentration of the starting material is 1% or less, which is unsatisfactory as an industrial preparation process.

An object of the present invention is to provide an industrially advantageous process for the preparation of an optically active 2-halo-1-(substituted phenyl)ethanol which is useful as medicines, agricultural chemicals or intermediates thereof. Another object of the present invention is to provide a simple process for the preparation of an optically active substituted styrene oxide or optically active 2-amino-1-(substituted phenyl)ethanol.

SUMMARY OF THE INVENTION

The inventors of the present invention made extensive studies to solve the aforementioned problems. As a result, it was found that optically active 2-halo-1-(substituted phenyl) ethanol compounds can be obtained by subjecting a 2-halo-1-(substituted phenyl)ethanol (I) to stereoselective esterification in the presence of an enzyme so that it is optically resolved into an optically active 2-halo-1-(substituted phenyl)ethanol ester (VI) and an optically active 2-halo-1-(substituted phenyl)ethanol (II) as an antipode and then separating and collecting each of these optically active compounds. It was also found that an optically active 2-amino-1-(substituted phenyl)ethanol (V) useful as medicines can be easily obtained by treating the optically active 2-halo-1-(substituted phenyl)ethanol (II) with a base to effect ring-closure and then reacting the resulting optically active substituted styrene oxide (IV) with an amine compound. The present invention was accomplished based on these findings.

Thus, the gist of the present invention resides in a process for producing an optically active 2-halo-1-(substituted phenyl)ethanol represented by the general formula (II):

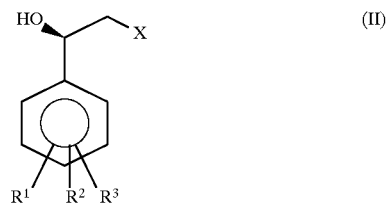

(wherein X represents a chlorine atom or a bromine atom, and $R^1$, $R^2$ and $R^3$ may be the same or different and each represent a hydrogen atom, a halogen atom, a $C_{1-5}$ alkyl group, a $C_{1-5}$ haloalkyl group, a $C_{1-5}$ alkoxy group, a cyano group or a nitro group, with the proviso that when two of $R^1$, $R^2$ and $R^3$ are alkyl groups or alkoxy groups, they may be combined together to form a ring and that all of $R^1$, $R^2$ and $R^3$ are not hydrogen atoms at the same time), which comprises allowing a 2-halo-1-(substituted phenyl)ethanol represented by the general formula (I):

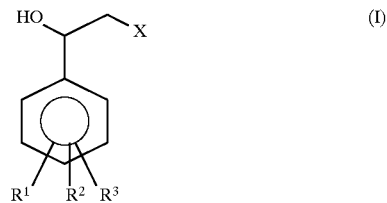

(wherein X, $R^1$, $R^2$ and $R^3$ are as defined above) to contact with an enzyme stereoselectively catalyzing ester interchange, in the presence of a carboxylic anhydride; a process for producing an optically active substituted styrene oxide (IV), which comprises treating the optically active 2-halo-1-(substituted phenyl)ethanol (II) obtained in the above process with a base; and a process for producing an optically active 2-amino-1-(substituted phenyl)ethanol (V), which comprises treating the optically active substituted styrene oxide (IV) obtained in the above process with an amine.

DETAILED DESCRIPTION OF THE INVENTION

Hereinafter, the present invention will be further described.

(1) Process for the preparation of an optically active 2-halo-1-(substituted phenyl)ethanol (II)

The preparation process of the present invention is carried out by allowing an enzyme stereoselectively catalyzing ester interchange to act on a 2-halo-1-(substituted phenyl)ethanol represented by the following general formula (I) and a carboxylic anhydride as an acyl donor. In this reaction, only (S)-form of 2-halo-1-(substituted phenyl)ethanol is esterified while (R)-form thereof is obtained as such, i.e., in the form of alcohol, which is shown by the following reaction scheme 1. The reaction mixture thus obtained can be subjected to separation as necessary to provide each of the optically active compounds having a high purity.

Reaction Scheme 1

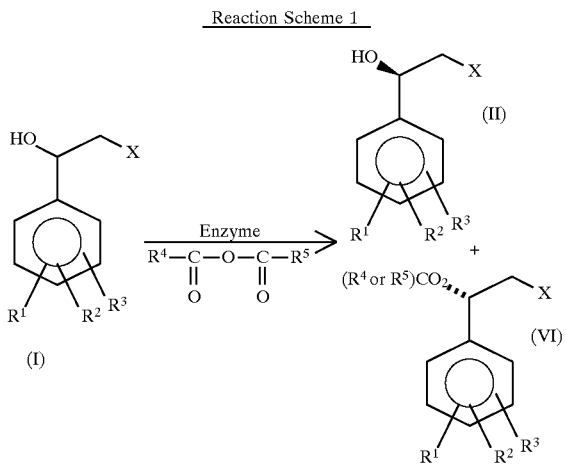

The compound represented by the foregoing general formula (VI) can be deprotected with its stereostructure being maintained to produce an optically active alcohol in (S)-form which can be used in various reactions. Alternatively, the compound (VI) can be racemized using an acid catalyst in a protic solvent to produce the starting material (I) in the reaction 1 (i.e., recycling).

As the starting material to be used in the preparation process of the present invention, the compound represented by the following general formula (I):

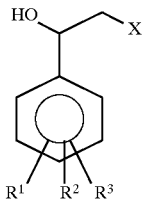

is used.

In the foregoing general formula (I), X represents a chlorine atom or a bromine atom, and $R^1$, $R^2$ and $R^3$ each represent a hydrogen atom; a halogen atom such as chlorine, bromine and iodine; a $C_{1-5}$ alkyl group such as methyl, ethyl, n-propyl, i-propyl, n-butyl, t-butyl and n-pentyl; a $C_{1-5}$ haloalkyl group such as fluoromethyl, difluoromethyl, trifluoromethyl and trichloroethyl; a $C_{1-5}$ alkoxy group such as methoxy, ethoxy, propoxy, isopropoxy, 2,2-dimethylpropoxy, butoxy, 2-methylbutoxy and pentoxy; a cyano group; or a nitro group. Among the groups represented by $R^1$, $R^2$ or $R^3$, a halogen atom, a $C_{1-5}$ alkyl group, a $C_{1-2}$ haloalkyl group or a $C_{1-5}$ alkoxy group, particularly a halogen atom. $R^1$, $R^2$ and $R^3$ may be the same or different from each other. If two of $R^1$, $R^2$ or $R^3$ are alkyl or alkoxy groups, they may be combined together to form an alkylene group, an alkyleneoxy group or an alkylenedioxy group. $R^1$, $R^2$ and $R^3$ are not hydrogen atoms at the same time (i.e., at least one of $R^1$, $R^2$ and $R^3$ is not a hydrogen atom).

Specific examples of the 2-halo-1-(substituted phenyl) ethanol to be used in the present invention include:

2-bromo-1-(3-chlorophenyl)ethanol,
2-bromo-1-(3-bromophenyl)ethanol,
2-bromo-1-(4-bromophenyl)ethanol,
2-bromo-1-(4-fluorophenyl)ethanol,
2-bromo-1-(3-iodophenyl)ethanol,
2-bromo-1-(3,5-dichlorophenyl)ethanol,
2-bromo-1-(3-trifluoromethylphenyl)ethanol,
2-bromo-1-(3-methoxyphenyl)ethanol,
2-bromo-1-(4-methoxyphenyl)ethanol,
2-bromo-1-(3,4-methylenedioxyphenyl )ethanol,
2-bromo-1-(4-cyanophenyl)ethanol,
2-bromo-1-(4-nitrophenyl)ethanol,
2-chloro-1-(3-chiorophenyl)ethanol,
2-chloro-1-(3-bromophenyl)ethanol,
2-chloro-1-(4-bromophenyl)ethanol,
2-chloro-1-(4-fluorophenyl)ethanol,
2-chloro-1-(3-iodophenyl)ethanol,
2-chloro-1-(3,5-dichlorophenyl)ethanol,
2-chloro-1-(3-trifluoromethylphenyl)ethanol,
2-chloro-1-(3-methoxyphenyl)ethanol,
2-chloro-1-(4-methoxyphenyl)ethanol,
2-chloro-1-(3,4-methylenedioxyphenyl)ethanol,
2-chloro-1-(4-cyanophenyl)ethanol, and
2-chloro-1-(4-nitrophenyl)ethanol. Among these compounds,
2-bromo-1-(3-chlorophenyl)ethanol,
2-bromo-1-(3-bromophenyl)ethanol,
2-bromo-1-(4-bromophenyl)ethanol,
2-bromo-1-(4-fluorophenyl)ethanol,
2-bromo-1-(3-iodophenyl)ethanol,
2-bromo-1-(3,5-dichlorophenyl)ethanol,
2-bromo-1-(3-trifluoromethylphenyl)ethanol,
2-bromo-1-(3-methoxyphenyl)ethanol,
2-bromo-1-(4-methoxyphenyl)ethanol,
2-bromo-1-(3,4-methylenedioxyphenyl)ethanol,
2-chloro-1-(3-chlorophenyl)ethanol,
2-chloro-1-(3-bromophenyl)ethanol,
2-chloro-1-(4-bromophenyl)ethanol,
2-chloro-1-(4-fluorophenyl)ethanol,
2-chloro-1-(3-iodophenyl)ethanol,
2-chloro-1-(3,5-dichlorophenyl)ethanol,
2-chloro-1-(3-trifluoromethylphenyl)ethanol,
2-chloro-1-(3- methoxyphenyl)ethanol,
2-chloro-1-(4-methoxyphenyl)ethanol, and
2-chloro-1-(3,4-methylenedioxyphenyl)ethanol are preferable. In addition,
2-bromo-1-(3-chlorophenyl)ethanol,
2-bromo-1-(3-bromophenyl)ethanol,
2-bromo-1-(4-bromophenyl)ethanol,
2-bromo-1-(4-fluorophenyl)ethanol,
2-bromo-1-(3-iodophenyl)ethanol,
2-chloro-1-(3-chlorophenyl)ethanol,
2-chloro-1-(3-bromophenyl)ethanol,
2-chloro-1-(4-bromophenyl)ethanol,
2-chloro-1-(4-fluorophenyl)ethanol, and
2-chloro-1-(3-iodophenyl)ethanol are particularly preferable.

The compound represented by the general formula (I) to be used in the present invention can be easily synthesized, e.g., by the hydrolysis of a 1,2-dihalo-1-substituted phenylethane in an aqueous solution, optionally using iodide as a catalyst, or the reduction of an acetophenone compound with sodium borohydride or the like.

As the carboxylic anhydride to be used in the preparation process of the present invention, the compound represented by the following general formula (III):

is used.

In the general formula (III), $R^4$ and $R^5$ each independently represent a $C_{1-20}$ straight-chain or branched alkyl or alkenyl group which may be substituted by one or more (preferably, one) substituents selected from the group consisting of a halogen atom, a $C_{1-5}$ alkoxy group, a $C_{1-5}$ acyl group or an aromatic group having 6 to 10 carbon atoms in which 1 to 3 of carbon atoms may be replaced by any of N, O and S ("N" represents an nitrogen atom, "O" represents an oxygen atom, and "S" represents an sulfur atom); or an aromatic group having 6 to 10 carbon atoms in which 1 to 3 of carbon atoms may be replaced by any of N, O and S, which may be substituted by one or more (preferably, one) substituents selected from the group consisting of a halogen atom, a $C_{1-5}$ alkoxy group and a $C_{1-5}$ acyl group. $R^4$ and $R^5$ may be combined together to form a ring. Preferable rings formed by combining $R^4$ and $R^5$ are saturated or unsaturated (preferably saturated) rings which have 2 to 3 carbon atoms as the moiety formed by $R^4$ and $R^5$. Among the groups represented by $R^4$ or $R^5$, preferable groups are a $C_{1-20}$ straight-chain or branched alkyl or alkenyl group which may be substituted by one or more (preferably, one) substituents selected from the group consisting of a halogen atom, a $C_{1-5}$ alkoxy group, a $C_{1-5}$ acyl group and a phenyl group; and a phenyl or pyridyl group which may be substituted by one or more (preferably, one) halogen atoms. Particularly preferable group is a $C_{1-12}$ straight-chain alkyl group.

Examples of the "halogen atom" include chlorine and bromine. Examples of the "$C_{1-5}$ alkoxy group" include methoxy, ethoxy, propoxy, isopropoxy, 2,2-dimethylpropoxy, butoxy, 2-methylbutoxy, and pentoxy. Examples of the "acyl group" include formyl, acetyl, propionyl, butyryl, isobutyryl, pivaloyl, acryloyl, methacryloyl, crotonoyl, and isocrotononyl. Examples of the "aromatic group having from 6 to 10 carbon atoms in which 1 to 3 of carbon atoms may be replaced by any of N, O and S" include phenyl and pyridyl.

Examples of the "$C_{1-20}$ straight-chain or branched alkyl group" include methyl, ethyl, n-propyl, n-butyl, t-butyl, n-pentyl, 2-ethylpentyl, n-hexyl, n-heptyl, n-undecyl, n-tridecyl, n-pentadecyl, and n-heptadecyl. Examples of the $C_{1-20}$ straight-chain or branched alkenyl include vinyl, 1-propenyl, isopropenyl, 1-butenyl, 2-(1-butenyl), 2-(2-butenyl), 1-pentenyl, 2-(1-pentenyl), 2-(2-pentenyl), 1-hexenyl, 2-(1-(4-methylpentenyl), and 2-(2-(4-methylpentenyl). Examples of the "aromatic group having from 6 to 10 carbon atoms 1 to 3 of which may be replaced by any of N, O and S" include phenyl and pyridyl.

Illustrative examples of the carboxylic anhydride include acetic anhydride, chloroacetic anhydride, bromoacetic anhydride, methoxyacetic anhydride, ethoxyacetic anhydride, phenylacetic anhydride, chlorophenylacetic anhydride, propionic anhydride, chloropropionic anhydride, butyric anhydride, isobutyric anhydride, valeric anhydride, isovaleric anhydride, caproic anhydride, caprylic anhydride, capric anhydride, lauric anhydride, acrylic anhydride, methacrylic anhydride, crotonic anhydride, benzoic anhydride, chlorobenzoic anhydride, picolinic anhydride, and chloropicolinic anhydride. Illustrative examples of the carboxylic anhydride in which $R^4$ and $R^5$ are combined together include succinic anhydride, maleic anhydride, glutaric anhydride, and phthalic anhydride. Among these carboxylic anhydrides, acetic anhydride, propionic anhydride, butyric anhydride, isobutyric anhydride, valeric anhydride, isovaleric anhydride, caproic anhydride, caprylic anhydride, capric anhydride, and lauric anhydride are preferable. Further, acetic anhydride, propionic anhydride, butyric anhydride, valeric anhydride, caproic anhydride, caprylic anhydride, and capric anhydride are more preferable from the standpoint of reaction rate, ease in repeated use of enzyme and simplicity of post-treatment.

The carboxylic anhydride is used in 0.5 to 100 equivalents based on racemic modification of 2-halo-1-(substituted phenyl)ethanol (I).

Any enzymes which can stereoselectively catalyzes ester interchange with respect to 2-halo-1-(substituted phenyl) ethanol may be used as the enzyme in the present invention. The enzyme is used preferably from 0.01 to 200% by weight (more preferably, from 1 to 50% by weight) based on the racemic starting compound (I). Examples of such an enzyme include lipase, esterase, and the like. Lipase and esterase are preferably those derived from microorganisms. Particularly preferred examples of such an enzyme include lipase derived from microorganisms belonging to the genera Pseudomonas, Alcaligenes, Achromobacter, Candida or Rhizopusu. Among these enzymes, lipase derived from microorganisms belonging to the genus Pseudomonas or Alcaligenes are particularly preferable from the standpoint of reactivity and selectivity of optional isomers.

Specific examples of the lipase derived from microorganisms belonging to Pseudomonas include TOYOCHIMU LIP (immobilized lipase available from Toyobo Co., Ltd.), Lipase PS (available from Amano Pharmaceutical Co., Ltd.), and Lipase AK (available from Amano Pharmaceutical Co., Ltd.). Specific examples of the lipase derived from microorganisms belonging to Alcaligenes include Lipase PL (available from Meito Sangyo Co., Ltd.), and Lipase QL (available from Meito Sangyo Co., Ltd.). These enzymes may include an freeze-dried enzyme or acetone-treated and dried enzymes from microorganism cells, or a treated microorganisms (e.g., microorganism disrupted by ultrasonic treatment), or culture broth, or culture broth supernatant, or crude enzyme, or purified enzyme, or the like.

These enzymes may be those produced by recombinant microorganisms designed with a proper expression system using a genetic recombination technology to produce the aforementioned natural enzymes.

In order to enhance the enzymatic activity and the stereoselectivity in the enzymatic reaction and hence increase the productivity and the optical purity of the reaction product, it is preferable to add a sucrose fatty acid ester in an amount of from 0.01 to 100% by weight based on the enzyme during the immobilization of the enzyme or during the reaction by the enzyme. Examples of the sucrose fatty acid ester include partial ester of sucrose with one or more of $C_{10-24}$ higher fatty acids (e.g., stearic acid, lauric acid, palmitic acid, behenic acid and myristic acid).

The immobilization of the enzyme is carried out, for example, as follows. A 0.01 to 1% by weight of sugar ester is dissolved in a 0.001M to 0.1M buffer. Then, an enzyme in an amount of from 0.1 to 20 parts by weight based on 1 part by weight of sugar ester is added, and the mixture is stirred for 1 hour to 2 days. A carrier for enzyme immobilization in an amount of 1 to 1000 parts by weight based on 1 part by weight of the enzyme is added to the mixture. After 1 to 7 days of adsorption of the enzyme, the carrier is dried to prepare an enzyme-immobilized carrier. Any buffers suitable for expressing activities of the enzyme may be used. The buffer has pH of from 4 to 10, preferably 6 to 9, and the temperature of from 1° C. to 50° C., preferably 4° C. to 20° C.

During enzymatic reaction, one or more of hydrophobic porous material, disaccharides, surfactants, etc. may be added.

Examples of the hydrophobic porous materials include Molecular Sieves, activated carbons, Celite, and the like. The hydrophobic porous material may be added in an amount of from 0.1 to 100 parts by weight based on 1 part by weight of the enzyme.

Examples of the disaccharides include lactose, sucrose, maltose, trehalose, and the like. The disaccharide may be added in an amount of from 0.1 to 100 parts by weight based on 1 part by weight of the enzyme.

Examples of the surfactants include CHAPS (Nakarai Tesque Co.), Nonidet P-40 and Brij 58 (Sigma Co.), n-octyl-b-thioglucoside and n-heptyl-b-thioglucoside (Dojindo Laboratories), Tween 20, Tween 40 and Tween 80 (Kao Corporation), Triton X-100 and Triton N-101 (Aldrich Co.), and the like. The surfactant may be used in an amount of from 0.01 to 100% by weight based on the weight of the enzyme.

The aforementioned reaction is carried out in the absence or presence of an organic solvent. It is preferable to use a solvent in order to keep the activity of the enzyme. The organic solvent to be used in the reaction is not specifically limited. Examples of the organic solvent employable in the present invention include ether solvents such as diethyl ether, diisopropyl ether, t-butyl methyl ether, dibutyl ether and tetrahydrofuran; hydrocarbon solvents such as hexane, heptane, isooctane, toluene and xylene; ester solvents such as methyl acetate and ethyl acetate; ketone solvents such as acetone, methyl ethyl ketone and methyl isobutyl ketone; halogen-type solvents such as chloroform and dichloromethane; dimethylformamide; dimethyl sulfoxide; and N-methyl pyrrolidone. Among these organic solvents, ether solvents and hydrocarbon solvents are preferably used.

The amount of the organic solvent to be used is normally 0 to 100 times by weight (from the standpoint of productivity, preferably from 0.01 to 20 times by weight, particularly from 0.05 to 10 times by weight) the weight of 2-halo-1-(substituted phenyl)ethanol represented by the general formula (I). In accordance with the preparation process of the present invention, the reaction can proceed effectively even in a relatively high organic solvent concentration.

The reaction may be carried out by suspending an enzyme stereoselectively catalyzing ester interchange in a mixture of a 2-halo-1-(substituted phenyl)ethanol (I) and a carboxylic anhydride (III) as an acyl donor and stirring or shaking the suspension, or by filling the enzyme on column and passing the aforementioned mixture through the column. After the completion of the reaction, the enzyme is removed by filtration or centrifugal separation. The filtrate is concentrated and then purified by, extraction, distillation, column chromatography, etc. to respectively obtain an optically active 2-halo-1-(substituted phenyl)ethanol compound (II) and an optically active 2-halo-1-(substituted phenyl)ethanol ester (VI) in a high purity. The enzyme thus recovered as it is can be used again for the subsequent enzymatic reaction.

The reaction is effected in either in aerobic atmosphere or in anaerobic atmosphere. The reaction temperature is normally from 0° C. to 100° C., preferably from 20° C. to 50° C. The reaction time is normally from 1 hour to several days.

The optical purity of the optically active 2-halo-1-(substituted phenyl)ethanol (II) obtained by the reaction of the present invention can be determined by a high performance liquid chromatography (column: Chiralcel-OJ, available from Daicel Chemical Industries, Ltd.; eluant: 10:1 to 50:1 mixture of hexane and isopropanol; flow rate: 1.0 me/min.; detection: 220 nm).

The optically active 2-halo-1-(substituted phenyl)ethanol ester (VI) by-produced by the foregoing enzymatic reaction is normally separated from the reaction system after the termination of the enzymatic reaction or the ring-closure reaction described below. The by-product thus separated is then deprotected to form an optically active alcohol and the optically active alcohol can be racemized in the presence of an acid catalyst in a protic solvent to convert itself into a compound represented by the general formula (I), which may be recycled.

The protic solvent in which the deprotection reaction is effected is not specifically limited. Water or an alcohol solvent such as methanol, ethanol, propanol and butanol is desirable. Such a protic solvent is preferably used in an amount of not less than equimolar with the optically active 2-halo-1-(substituted phenyl)ethanol ester.

The acid catalyst is not specifically limited. Examples of the acid catalyst to be used in the present invention include Bronsted acid such as sulfuric acid, nitric acid, hydrochloric acid, hydrobromic acid, acetic acid, trifluoroacetic acid, phosphoric acid, methanesulfonic acid and p-toluenesulfonic acid; and Lewis acid such as zinc chloride, aluminum chloride, titanium tetrachloride, tin chloride and boron trifluoride. Bronsted acids are preferable. Sulfuric acid, trifluoroacetic acid, methanesulfonic acid or p-toluenesulfonic acid, which can also be used in the racemization reaction described later, are particularly preferable. The most desirable acid catalyst is sulfuric acid, which is inexpensive and can be easily used on an industrial basis. The amount of the acid catalyst to be used is preferably not less than 0.001 mol based on the ester as a starting material.

The reaction of the present invention can be effected at atmospheric pressure or under pressure. The reaction temperature is normally from −20° C. to 200° C., preferably from 0° C. to 150° C., particularly from 20° C. to 120° C. The reaction is effected for 5 minutes to 100 hours.

The subsequent racemization reaction is effected in an aqueous solvent, i.e., in a water alone or in a mixture of water and an organic solvent. The organic solvent is selected from an alcohol solvent such as methanol, ethanol, propanol and butanol; hydrocarbon solvent such as hexane, heptane, isooctane, benzene and toluene; ether solvent such as diethyl ether, diisopropyl ether, dibutyl ether and t-butyl methyl ether; halogen-type solvent such as dichloromethane, chloroform and dichloroethane; or ester solvent such as methyl acetate, ethyl acetate, methyl propionate, methyl butyrate, methyl valerate and methyl caproate may be present in the reaction system as well. Among these organic solvents, hydrocarbon solvents, halogen-type solvents and mixture thereof are preferable. The amount of such an aqueous solvent to be used is from 0.01 to 100 times the weight of the optically active 2-halo-1-(substituted phenyl)ethanol.

As the acid catalyst, a Bronsted acid is normally used. In particular, sulfuric acid, trifluoroacetic acid, methanesulfonic acid and p-toluenesulfonic acid are desirable. In this case, if the catalyst concentration is low with respect to water, the racemization rate is low. On the contrary, if the catalyst concentration is high with respect to water, it involves the decomposition of the optically active 2-halo-1-(substituted phenyl)ethanol as a starting material. Accordingly, when an aqueous sulfuric acid is used, it is normally used in a concentration of from 20 to 80% by weight, preferably from 30 to 70% by weight, more preferably from 40 to 60% by weight.

After the termination of the foregoing deprotection reaction or racemization reaction, the reaction system can be subjected to salting-out or extraction to isolate the reaction product which is then purified by distillation or column chromatography. By appropriately selecting the solvent and the catalyst in the foregoing reaction, the deprotection reaction can be directly followed by the racemization reaction without isolating (S)-2-halo-1-(substituted phenyl) ethanol obtained in the deprotection reaction.

(2) Process for the preparation of an optically active substituted styrene oxide The optically active 2-halo-1-(substituted phenyl)ethanol (II) obtained by the foregoing enzymatic reaction can be subjected to ring closure reaction by the treatment with a base to convert it into an optically active substituted styrene oxide represented by the following general formula (IV):

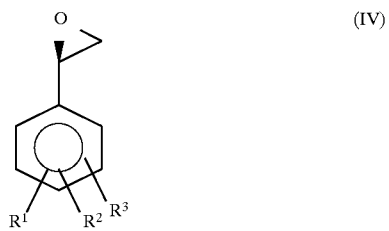

(IV)

wherein $R^1$, $R^2$ and $R^3$ are as defined in the general formula (I). The foregoing enzymatic reaction gives an optically active 2-halo-1-(substituted phenyl)ethanol ester (VI) as a by-product. In this process, the by-product may be subjected to reaction as it is in admixture with the optically active 2-halo-1-(substituted phenyl)ethanol (II), which is advantageous on an industrial basis since the step of isolation and purification can be eliminated.

Examples of the base to be used in the ring-closure reaction include inorganic bases such as hydroxide of alkaline metal (e.g., sodium hydroxide, potassium hydroxide) and carbonate of alkaline metal (e.g., sodium carbonate, potassium carbonate, sodium hydrogencarbonate), and organic bases such as alkoxide of alkaline metal (e.g., sodium methoxide, sodium ethoxide, sodium t-butoxide, potassium t-butoxide) and amine compound (e.g., butylamine, dibutylamine, triethylamine, 1,4-diazabicyclo[2,2,2]octane (DABCO), 1,8-diazabicyclo[5.4.0]undec-7-ene (DBU), 1,5-diazabicyclo[4,3,0]non-5-ene (DBN)). Among these bases, inorganic bases are preferable from the standpoint of reaction yield and simplicity of post-treatment. In particular, hydroxides or carbonates of alkaline metal are desirably used. The amount of the base to be used is from 1 to 10 equivalents, preferably from 1 to 5 equivalents based on the optically active 2-halo-1-(substituted phenyl)ethanol (II).

The ring-closure reaction is carried out in the absence or presence of solvent. The solvent to be used in the reaction is not specifically limited. Examples of the solvent to be used include ether solvents such as diethyl ether, diisopropyl ether, t-butyl methyl ether, dibutyl ether and tetrahydrofuran; hydrocarbon solvents such as hexane, heptane, isooctane, toluene and xylene; ester solvents such as methyl acetate and ethyl acetate; ketone solvents such as acetone, methyl ethyl ketone and methyl isobutyl ketone; halogen-type solvents such as chloroform and dichloromethane; dimethylformamide; dimethyl sulfoxide; and N-methyl pyrrolidone. Among these solvents, ether solvents and hydrocarbon solvents are preferable. The solvent to be used in the ring-closure reaction may be the same as or different from that used in the foregoing enzymatic reaction. The amount of the solvent to be used is from 0 to 100 times (from the standpoint of productivity, preferably from 0 to 20 times) the weight of the optically active 2-halo-1-(substituted phenyl) ethanol (II).

The ring-closure reaction is carried out at atmospheric pressure or under pressure. The reaction is effected normally at a temperature of from −50° C. to 150° C., preferably from 0° C. to 50° C. for 5 minutes to 24 hours, though they may vary depending on the kind of the base used.

After the termination of the reaction, the resulting optically active substituted styrene oxide (IV) can be isolated by any simple method such as distillation. The optical purity of the optically active substituted styrene oxide obtained by the reaction of the present invention can be determined by a high performance liquid chromatography (column: ChiralpackAD, available from Daicel Chemical Industries, Ltd.; eluant: 1,000:0.4 mixture of hexane and isopropanol; flow rate: 1.0 ml/min.; detection: 220 nm).

If the reaction is carried out in the presence of the optically active 2-halo-1-(substituted phenyl)ethanol ester (VI) as a by-product of the foregoing enzymatic reaction, the ethanol ester is separated as a high boiling point product in distillation. Thus, the ethanol ester separated can be subjected to the foregoing deprotection reaction and racemization reaction to convert it into a 2-halo-1-(substituted phenyl)ethanol (I) which can be recycled for enzymatic reaction as a starting material.

(3) Process for the preparation of an optically active 2-amino-1-(substituted phenyl)ethanol The optically active substituted styrene oxide (IV) obtained by the foregoing reaction can be reacted with an amine compound to convert it into an 2-amino-1-(substituted phenyl)ethanol represented by the following general formula (V):

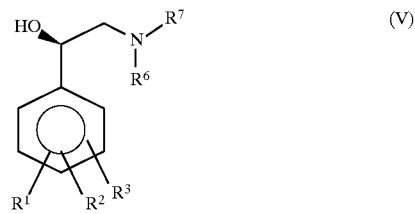

(V)

(wherein $R^6$ and $R^7$ each independently represent a hydrogen atom or a $C_{1-10}$ straight-chain or branched alkyl group which may be substituted by an aromatic group, which aromatic group may further be substituted by a halogen atom, a hydroxyl group, a $C_{1-10}$ alkyl group, a $C_{1-10}$ alkoxy group or a $C_{1-10}$ alkoxycarbonyl group).

The amine compound to be used herein is not specifically limited as long as it is ammonia or primary or secondary amine which can react with styrene oxide. It is preferably ammonia or $C_{1-10}$ straight-chain or branched alkylamine. The alkylamine may be substituted by an aromatic group such as a phenyl group and a pyridyl group, and the aromatic group may further be substituted by a halogen atom, a hydroxyl group, a $C_{1-10}$ alkyl group, a $C_{1-10}$ alkoxy group or a $C_{1-10}$ alkoxycarbonyl group. The carbon number of the alkoxycarbonyl group include the carbon atom of the carbonyl moiety.

The reaction of the amine compound with the foregoing styrene oxide can be easily accomplished by heating these compounds in a polar solvent such as dimethyl sulfoxide (Eur. J. Med. Chem., 29, 259–267 (1994), J. Med. Chem., 35, 3081–3084 (1992)).

The foregoing 2-amino-1-(substituted phenyl)ethanol (V) is useful as a medicine such as diabetic medicine and anti-obesity medicine, which is represented by the following general formula (VII). According to the present invention, these compounds can be efficiently synthesized from the inexpensive and safe starting materials with an easy procedure.

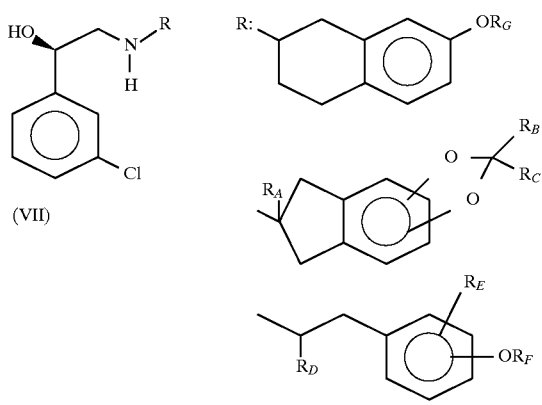

(see, Eur. J. Med. Chem. (1994) 29, 259–267, EP-A1-608568, J. Med. Chem., 1992, 35, 3081–3084, EP-A1-170121, and EP-A1-28105 with respect to the substituents $R_A$ to $R_G$.)

The present invention will be further described by way of Examples, but the present invention should not be construed as being limited thereto.

In the following Examples, the optical purity of the optically active 2-halo-1-(substituted phenyl)ethanol (II) was determined by a high performance liquid chromatography (column: Chiralcel-OJ, available from Daicel Chemical Industries, Ltd.; eluant: 10:1 to 50:1 mixture of hexane and isopropanol; flow rate: 1.0 ml/min.; detection: 220 nm). The optical purity of the optically active substituted styrene oxide was determined by a high performance liquid chromatography (column: ChiralpackAD, available from Daicel Chemical Industries, Ltd.; eluant: 1,000:0.4 mixture of hexane and isopropanol; flow rate: 1.0 ml/min.; detection: 220 nm).

PREPARATION EXAMPLE 1

Synthesis of 2-bromo-1-(3-chlorophenyl)ethanol

To 996 g of 3-chloro-α,β-dibromoethylbenzene were added 10.8 g of potassium iodide and 3.5 l of water. The mixture was then heated under reflux for 49 hours while the released free iodine was being removed. After the termination of the reaction, the reaction solution was allowed to cool to room temperature. The oil phase separated was separated and then washed with water for neutralization to give 714 g of 2-bromo-1-(3-chlorophenyl)ethanol was obtained.

EXAMPLE 1

Synthesis of (R)-2-bromo-1-(3-chlorophenyl)ethanol

To 100 mg (0.4 mmol) of 2-bromo-1-(3-chlorophenyl)ethanol were added 30 mg of Lipase QL (available from Meito Sangyo Co., Ltd.) and 40 mg (0.4 mmol) of acetic anhydride. Diisopropyl ether was added to the mixture to make the total volume to 1 ml. The reaction mixture was then allowed to undergo reaction at a temperature of 35° C. for 72 hours. After the termination of the reaction, the enzyme was removed by filtration. The resulting filtrate was then concentrated under reduced pressure. The concentrated solution was analyzed by $^1$H-NMR. As a result, it was found that (R)-2-bromo-1-(3-chlorophenyl) ethanol and (S)-2-bromo-1-(3-chlorophenyl)ethyl acetate had been produced in a proportion of 2:3. The concentrated solution was then separated by a thin layer silica gel chromatography. As a result, (R)-2-bromo-1-(3-chlorophenyl)ethanol ($[\alpha]_D^{20}$=−25.6°, C=1.05) and (S)-2-bromo-1-(3-chlorophenyl)ethyl acetate ($[\alpha]_D^{20}$=+40.4°, C=0.60) were obtained. The optical purity of (R)-2-bromo-1-(3-chlorophenyl)ethanol thus obtained was analyzed by Chiral HPLC. The results were 100% ee.

EXAMPLES 2 AND 3

The foregoing reaction procedure was repeated except that the amount of Lipase QL was changed to 10 mg and 39 mg (0.3 mmol) of propionic anhydride or 47 mg (0.3 mmol) of butyric anhydride was used as the acid anhydride. The results of these reactions are set forth in Table 1

TABLE 1

| Example No. | Acylating agent | Optical purity | % Conversion |
|---|---|---|---|
| 2 | Propionic anhydride | 99.7% ee | 51.2 |
| 3 | Butyric anhydride | 99.4% ee | 54.4 |

EXAMPLES 4 to 8

Synthesis of (R)-2-bromo-1-(3-chlorophenyl)ethanol

The reaction procedure of Example 2 was repeated except that each of the various acid anhydrides shown in Table 2 was used in an amount of 0.3 mmol and the reaction time was changed to 122 hours. The results are set forth in Table 2.

TABLE 2

| Example No. | Acylating agent | Optical purity | % Conversion |
|---|---|---|---|
| 4 | Isobutyric anhydride | 99.8% ee | 55.8 |
| 5 | Valeric anhydride | 90.1% ee | 50.1 |
| 6 | Isovaleric anhydride | 73.2% ee | 43.9 |
| 7 | n-Caproic anhydride | 83.7% ee | 50.9 |
| 8 | n-Caprylic anhydride | 89.4% ee | 50.1 |

EXAMPLES 9 to 16

Synthesis of (R)-2-bromo-1-(3-chlorophenyl)ethanol

Diisopropyl ether was added to a mixture of 100 mg (0.4 mmol) of 2-bromo-1-(3-chlorophenyl)ethanol, 20 mg of TOYOCHIMU LIP (available from Toyobo Co., Ltd.) and 0.3 mmol of each of the various acid anhydrides shown in Table 3 was to make the total volume to 1 ml. These reaction mixtures were respectively allowed to undergo reaction at a temperature of 27° C. for 98 hours. The results are set forth in Table 3.

TABLE 3

| Example No. | Acylating agent | Optical purity | % Conversion |
|---|---|---|---|
| 9 | Acetic anhydride | 79.3% ee | 45.4 |
| 10 | Propionic anhydride | 99.0% ee | 54.4 |
| 11 | Butyric anhydride | 99.8% ee | 53.1 |
| 12 | Isobutyric anhydride | 95.3% ee | 52.8 |
| 13 | Valeric anhydride | 99.0% ee | 53.7 |
| 14 | Isovaleric anhydride | 98.8% ee | 50.3 |
| 15 | n-Caproic anhydride | 100% ee | 55.0 |
| 16 | n-Caprylic anhydride | 100% ee | 60.3 |

EXAMPLE 17 AND COMPARATIVE EXAMPLE 1

Synthesis of (R)-2-bromo-1-(3-chlorophenyl)ethanol

To a mixture of 100 mg (0.4 mmol) of 2-bromo-1-(3-chlorophenyl)ethanol, 10 mg of Lipase QL (Meito Sangyo Co., Ltd.) and 39 mg (0.3 mmol) of propionic anhydride or 30 mg (0.36 mmol) of vinyl propionate as an acylating agent was added t-butyl methyl ether to make the total volume to 1 ml. These reaction mixtures were respectively allowed to undergo reaction at a temperature of 35° C. for 22 hours. The results are set forth in Table 4.

TABLE 4

| Example No. | Acylating agent | Optical purity | % Conversion |
|---|---|---|---|
| 17 | Propionic anhydride | 96.0% ee | 50.8 |
| Comparative Example 1 | Vinyl propionate | 69.1% ee | 42.6 |

EXAMPLE 18 AND COMPARATIVE EXAMPLE 2

Synthesis of (R)-2-bromo-1-(3-chlorophenyl)ethanol

To a mixture of 100 mg (0.4 mmol) of 2-bromo-1-(3-chlorophenyl)ethanol, 10 mg of TOYOCHIMU LIP (available from Toyobo Co., Ltd.) and 100 mg (0.31 mmol) of n-caprylic anhydride or 61 mg (0.27 mmol) of vinyl laurate as an acylating agent was added isopropyl ether to make the total volume 1 ml. The reaction mixtures were respectively allowed to undergo reaction at a temperature of 27° C. for 30 hours. After the termination of the reaction, the reaction system was subjected to centrifugal filtration to remove the supernatant. To the reaction system was then added another batch of 2-bromo-1-(3-chlorophenyl)ethanol, the acylating agent and diisopropyl ether to make the total volume 1 ml. The same reaction was then repeated twice. The initial rate and total activity at the various steps are set forth in Table 5. The initial rate is represented relative to that at the 1st step as 100%. Activity=total amount of converted BH/enzyme weight.

TABLE 5

| | Acylating agent | | % Initial rate | Activity (g/g of enzyme) |
|---|---|---|---|---|
| Example 18 | Caprylic anhydride | 1st | 100 | 24.6 |
| | | 2nd | 72 | |
| | | 3rd | 62 | |
| Comparative Example 6 | Vinyl laurate | 1st | 100 | 16.0 |
| | | 2nd | 45 | |
| | | 3rd | 25 | |

EXAMPLES 19 to 24

Diisopropyl ether was added to a mixture of 5 mg of TOYOCHIMU LIP (available from Toyobo Co., Ltd.), 0.052 ml of caproic anhydride, 50 mg of 2-bromo-1-(3-chlorophenyl)ethanol (referred to as "BH" herein), and 5 mg of each of the following additives to make the total volume to 0.5 ml. These reaction mixtures were respectively allowed to undergo reaction at a temperature of 27° C. for 68 hours. The results are set forth in Table 6.

TABLE 6

| Example No. | Additive | Optical purity of BH |
|---|---|---|
| 19 | None | 95.2% ee |
| 20 | Sucrose (Wako Pure Chemicals) | 95.2% ee |
| 21 | Maltose (Wako Pure Chemicals) | 96.5% ee |
| 22 | Sugar Ester S370 (Mitsubishi Chemical Corporation) | 97.1% ee |
| 23 | Sugar Ester S570 (Mitsubishi Chemical Corporation) | 97.1% ee |
| 24 | CHAPS (Nakarai Tesque Co.) | 97.1% ee |

EXAMPLES 25 AND 26

Lipoprotein lipase (20 mg, available from Toyobo Co., Ltd.) and Sugar Ester S570 (5 mg, available from Mitsubishi Chemical Foods Co., Ltd.) were dissolved in 5 ml of 20 mM TES-Na buffer, and the solution was stirred at 4° C. for 20 hours. Then, Hyflo Super-Cel (2 g, available from Wako Pure Chemicals) was added to the solution to contact to the enzyme at 4° C. for 20 hours, followed by freeze-drying to obtain an immobilized lipase (hereinafter, referred to as "S570").

Diisopropyl ether was added to a mixture of 20 mg of the immobilized enzyme, 10 mg of Molecular Sieves 4A, 0.049 ml of butyric anhydride or 0.060 ml of caproic anhydride, and 100 mg of 2-bromo-1-(3-chlorophenyl)ethanol to make the total volume to 1.0 ml. These reaction mixtures were respectively allowed to undergo reaction at a temperature of 27° C. The same procedure was repeated except that the immobilized enzyme of replaced by 20 mg of TOYOCHIMU LIP. The results are set forth in Table 7.

TABLE 7

| Example No. | Acylating Agent | Enzyme | Optical Purity after 4 hours | Optical Purity after 20 hours |
|---|---|---|---|---|
| 25 | Butyric anhydride | S570 | 80.8% ee | 98.2% ee |
| | | TOYOCHIMU LIP | 55.8% ee | 93.9% ee |
| 26 | Caproic anhydride | S570 | 82.3% ee | 98.0% ee |
| | | TOYOCHIMU LIP | 57.6% ee | 90.7% ee |

EXAMPLE 27

Synthesis of (R)-3-chlorostyrene oxide

To a mixture of 50 g of 2-bromo-1-(3-chlorophenyl) ethanol, 10 g of Lipase QL (available from Meito Sangyo Co., Ltd.) and 19.5 g of propionic anhydride was added 330 ml of t-butyl methyl ether. The reaction mixture was then allowed to undergo reaction at a temperature of 35° C. for 22 hours. After the termination of the reaction, the lipase was removed by filtration. To the filtrate was then added 260 g of a 1M aqueous solution of sodium hydroxide. The mixture was then stirred at room temperature for 1 hour. After the termination of the reaction, the resulting organic phase was separated, and then washed with water and brine for neutralization. The reaction solution was then analyzed by gas chromatography. As a result, it was confirmed that (R)-3-chlorostyrene oxide and (S)-2-bromo-1-(3-chlorophenyl) ethyl propionate had been produced. It was also found that the percent conversion of (R)-2-bromo-1-(3-chlorophenyl) ethanol was 100% and the yield of (R)-3-chlorostyrene oxide was 98%. The organic phase was concentrated under reduced pressure, and then distilled to obtain 13.2 g of (R)-3-chlorostyrene oxide (boiling point: 77° C./3 mmHg; $[\alpha]_D^{20}=-11.6°$; C=0.40). The yield from this compound, 2-bromo-1-(3-chlorophenyl)ethanol, was 40.6%. The optical purity of (R)-3-chlorostyrene oxide was determined by a high performance liquid chromatography using an optically active column. The result was 98.6% ee.

EXAMPLE 28

Synthesis of (R)-3-chlorostyrene oxide

A 1:1 mixture (50 mg) of (R)-2-bromo-1-(3-chlorophenyl)ethanol and (S)-2-bromo-1-(3-chlorophenyl) ethyl acetate was dissolved in 2 ml of dichloromethane. Then, 1,8-diazabicyclo[5.4.0]undec-7-ene (DBU) (15 mg, which is equivalent to (R)-2-bromo-1-(3-chlorophenyl)

ethanol) was added. The reaction solution was then allowed to undergo reaction at room temperature for 30 minutes. The reaction solution was then analyzed by gas chromatography. As a result, it was found that (R)-3-chlorostyrene oxide had been produced in a yield of 88% with respect to (R)-2-bromo-1-(3-chlorophenyl)ethanol. It was also found that the percent conversion of (R)-2-bromo-1-(3-chlorophenyl) ethanol was 92%.

EXAMPLE 29

Synthesis of (R)-3-chlorostyrene oxide

A 1:1 mixture (50 mg) of (R)-2-bromo-1-(3-chlorophenyl)ethanol and (S)-2-bromo-1-(3-chlorophenyl) ethyl acetate was dissolved in 2 ml of dichloromethane. Then, 1,4-diazabicyclo[2,2,2]octane (DABCO) (11 mg, which is equivalent to (R)-2-bromo-1-(3-chlorophenyl) ethanol) was added. The reaction solution was then allowed to undergo reaction under reflux for 1 hour. The reaction solution was then analyzed by gas chromatography. As a result, it was found that (R)-3-chlorostyrene oxide had been produced in a yield of 6% with respect to (R)-2-bromo-1-(3-chlorophenyl)ethanol. It was also found that the percent conversion of (R)-2-bromo-1-(3-chlorophenyl)ethanol was 7%.

EXAMPLE 30

Synthesis of (R)-3-chlorostyrene oxide

A 1:1 mixture (50 mg) of (R)-2-bromo-1-(3-chlorophenyl)ethanol and (S)-2-bromo-1-(3-chlorophenyl) ethyl acetate was dissolved in 2 ml of dichloromethane. Then, triethylamine (10 mg, which is equivalent to (R)-2-bromo-1-(3-chlorophenyl)ethanol) was added. The reaction solution was then allowed to undergo reaction under reflux for 10 hours. The reaction solution was then analyzed by gas chromatography. As a result, it was found that (R)-3-chlorostyrene oxide had been produced in a yield of 32% with respect to (R)-2-bromo-1-(3-chlorophenyl)ethanol. It was also found that the percent conversion of (R)-2-bromo-1-(3-chlorophenyl)ethanol was 58%.

EXAMPLE 31

Synthesis of (R)-3-chlorostyrene oxide

A 1:1 mixture (50 mg) of (R)-2-bromo-1-(3-chlorophenyl)ethanol and (S)-2-bromo-1-(3-chlorophenyl) ethyl acetate was dissolved in 2 ml of dimethylformamide. Then, $K_2CO_3$ (14 mg, which is equivalent to (R)-2-bromo-1-(3-chlorophenyl)ethanol) was added. The reaction solution was then allowed to undergo reaction at a temperature of 50° C. for 2 hours. The reaction solution was then analyzed by gas chromatography. As a result, it was found that (R)-3-chlorostyrene oxide had been produced in a yield of 58% with respect to (R)-2-bromo-1-(3-chlorophenyl) ethanol. It was also found that the percent conversion of (R)-2-bromo-1-(3-chlorophenyl)ethanol was 92%.

The results of Examples 28 to 31 are set forth in Table 8.

TABLE 8

| Example No. | Base | Solvent | Reaction temperature (°C.) | Reaction time (hour) | % Conversion | % Yield |
| --- | --- | --- | --- | --- | --- | --- |
| 28 | DBU | $CH_2Cl_2$ | Room temperature | 0.5 | 92 | 88 |
| 29 | DABCO | $CH_2Cl_2$ | Refluxed | 1 | 7 | 6 |
| 30 | $Bt_3N$ | $CH_2Cl_2$ | Refluxed | 10 | 58 | 32 |
| 31 | $K_2CO_3$ | DMF | 50 | 2 | 92 | 58 |

In accordance with the present invention, an optically active 2-halo-1-(substituted phenyl)ethanol can be easily obtained by optionally resolving a 2-halo-1-(substituted phenyl)ethanol by using a specific enzyme. The optically active 2-halo-1-(substituted phenyl)ethanol can then be treated with a base after or without separation to obtain an optically active substituted styrene oxide, which may then be reacted with an amine compound to produce an optically active 2-amino-1-(substituted phenyl)ethanol. These compounds are useful as medicines, agricultural chemicals or intermediates thereof.

While the invention has been described in detail and with reference to specific embodiments thereof, it will be apparent to one skilled in the art that various changes and modifications can be made therein without departing from the spirit and scope thereof.

What is claimed is:

1. A process for p roducing an optically active 2-halo-1-(substituted phenyl)ethanol repr esented by the general formula (II):

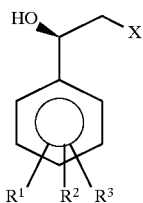

(II)

(wherein X represents a chlorine atom or a bromine atom, and $R^1$, $R^2$ and $R^3$ may be the same or different and each represent a hydrogen atom, a halogen atom, a $C_{1-5}$ alkyl group, a $C_{1-5}$ haloalkyl group, a $C_{1-5}$ alkoxy group, a cyano group or a nitro group, with the proviso that when two of $R^1$, $R^2$ and $R^3$ are alkyl groups or alkoxy groups, they may be combined together to form a ring and that all of $R^1$, $R^2$ and $R^3$ are not hydrogen atoms at the same time), which comprises allowing a 2-halo-1-(substituted phenyl)ethanol represented by the general formula (I):

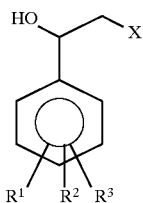

(I)

(wherein X, $R^1$, $R^2$ and $R^3$ are as defined above) to contact with an enzyme stereoselectively catalyzing ester interchange, in the presence of a carboxylic anhydride.

2. The process according to claim 1, wherein $R^1$, $R^2$ and $R^3$ each independently represent a halogen atom, a $C_{1-5}$ alkyl group, a $C_{1-2}$ haloalkyl group or a $C_{1-5}$ alkoxy group.

3. The process according to claim 1, wherein said carboxylic anhydride is represented by the general formula (III):

(III)

wherein $R^4$ and $R^5$ each independently represent (1) a $C_{1-20}$ straight-chain or branched alkyl or alkenyl group which may be substituted by a substituent selected from the group consisting of a halogen atom, a $C_{1-5}$ alkoxy group, a $C_{1-5}$ acyl group and an aromatic group having 6 to 10 carbon atoms in which 1 to 3 carbon atoms may be replaced by any of N, O and S, or (2) an aromatic group having 6 to 10 carbon atoms in which 1 to 3 carbon atoms may be replaced by any of N, O and S, which may be substituted by a substituent selected from the group consisting of a halogen atom, a $C_{1-5}$ alkoxy group and a $C_{1-5}$ acyl group.

4. The process according to claim 3, wherein $R^4$ and $R^5$ each independently represent (1) a $C_{1-20}$ straight-chain or branched alkyl group which may be substituted by a substituent selected from the group constituting of a halogen atom, a $C_{1-5}$ alkoxy group, a $C_{1-5}$ acyl group and a phenyl group, (2) a $C_{1-10}$ straight-chain or branched alkenyl group, or (3) a phenyl or pyridyl group which may be substituted by a halogen atom.

5. The process according to claim 1, wherein said enzyme is lipase derived from microorganism.

6. The process according to claim 1, wherein said enzyme is lipase derived from a microorganism belonging to genus Pseudomonas or Alcaligenes.

7. A process for producing an optically active substituted styrene oxide represented by the general formula (IV):

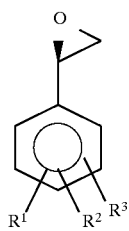

(IV)

(wherein $R^1$, $R^2$ and $R^3$ may be the same or different and each represent a hydrogen atom, a halogen atom, a $C_{1-5}$ alkyl group, a $C_{1-5}$ haloalkyl group, a $C_{1-5}$ alkoxy group, a cyano group or a nitro group, with the proviso that when two of $R^1$, $R^2$ and $R^3$ are alkyl groups or alkoxy groups, they may be combined together to form a ring and that all of $R^1$, $R^2$ and $R^3$ are not hydrogen atoms at the same time), which comprises treating, with a base, an optically active 2-halo-1-(substituted phenyl)ethanol represented by the general formula (II) obtained by the process claimed in claim 1.

8. The process according to claim 5, wherein said base is an alkaline metal hydroxide or an alkaline metal carbonate.

9. A process for producing an optically active 2-amino-1-(substituted phenyl)ethanol represented by the general formula (V):

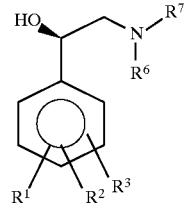

(V)

(wherein $R^1$, $R^2$ and $R^3$ may be the same or different and each represent a hydrogen atom, a halogen atom, a $C_{1-5}$ alkyl group, a $C_{1-5}$ haloalkyl group, a $C_{1-5}$ alkoxy group, a cyano group or a nitro group, with the proviso that when two of $R^1$, $R^2$ and $R^3$ are alkyl groups or alkoxy groups, they may be combined together to form a ring and that all of $R^1$, $R^2$ and $R^3$ are not hydrogen atoms at the same time; and $R^6$ and $R^7$ each independently represent a hydrogen atm or a $C_{1-10}$ straight-chain or branched alkyl group, which may be substituted by an aromatic group, which aromatic group may further be substituted by a hydrogen atom, a hydroxyl group, a $C_{1-10}$ alkyl group, a $C_{1-10}$ alkoxy group or a $C_{1-10}$ alkoxycarbonyl group), which comprises treating, with a base, an optically active 2-halo-1-(substituted phenyl)ethanol represented by the general formula (II) obtained by the process claimed in claim 1 to form an optical active substituted styrene oxide represented by the general fonnula (IV):

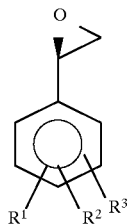

(IV)

(wherein $R^1$, $R^2$ and $R^3$ are as defined above), and reacting the optical active substituted styrene oxide represented by the general formula (IV) with an amine compound of fonnula $NHR^6R^7$, wherein $R^6$ and $R^7$ are as defined above.

* * * * *